United States Patent [19]

Ohkawa et al.

[11] 3,974,178
[45] Aug. 10, 1976

[54] NAPHTHOSTYRIL CATIONIC DYES

[75] Inventors: Masaaki Ohkawa, Takatsuki; Seizo Konishi, Minoo; Kazuyoshi Hirabayashi, Takarazuka; Sadaharu Abeta, Toyonaka; Tetsuo Okaniwa, Minoo; Yoshiro Takeda, Takarazuka, all of Japan

[73] Assignee: Sumitomo Chemical Company, Limited, Osaka, Japan

[22] Filed: Mar. 21, 1973

[21] Appl. No.: 343,336

[30] Foreign Application Priority Data

Mar. 25, 1972 Japan.............................. 47-30109

[52] U.S. Cl.............................. 260/326.5 B; 8/84; 8/1 S; 260/326.5 SF
[51] Int. Cl.²...................................... C07D 209/92
[58] Field of Search.............. 260/326.5 B, 326.5 SF

[56] References Cited
UNITED STATES PATENTS
3,769,297   10/1973   Brack........................... 260/326.5 B FOREIGN PATENTS OR APPLICATIONS
2,018,863   6/1970   France
1,944,797   3/1971   Germany
1,017,267   1/1966   United Kingdom.......... 260/326.5 B OTHER PUBLICATIONS
Ohkawa et al., Chem. Abs., 80, 38381q (1974).

Primary Examiner—Alton D. Rollins
Assistant Examiner—Mark L. Berch
Attorney, Agent, or Firm—Sughrue, Rothwell, Mion, Zinn & Macpeak

[57] ABSTRACT

A compound of the formula (I):

$$\left[ R_1 - N^+ = C \underset{X_n}{\overset{Y_n}{\bigodot}} N \diagdown_{CH_2-CH-R_3}^{R_2} \right] Z^- \quad (I)$$

wherein
  $R_1$ is a $C_1$–$C_4$ alkyl or $C_1$–$C_2$ alkoxy- or cyano-substituted $C_1$–$C_4$ alkyl,
  $R_2$ is a $C_1$–$C_4$ alkyl, phenyl, $C_1$–$C_2$ alkoxy-substituted phenyl, $C_7$–$C_8$ aralkyl or cyclophenyl,
  $R_3$ is a $C_1$–$C_4$ alkyl, $C_1$–$C_4$ alkoxy-substituted $C_1$–$C_2$ alkyl or phenoxy-substituted $C_1$–$C_2$ alkyl,
  X is hydrogen, a halogen or N,N—di—$C_1$–$C_4$ alkylsulfonamide,
  Y is hydrogen, a $C_1$–$C_2$ alkyl or a halogen,
  n is an integer of from 1 to 2, and
  $Z^-$ is an anion,
which is useful for dyeing acid modified polyacrylonitrile, polyester or polyamide fibers with a high fastness and an excellent vividness.

5 Claims, No Drawings

NAPHTHOSTYRIL CATIONIC DYES

BACKGROUND OF THE INVENTION

1. Field of the Invention

The present invention relates to a novel cationic dye for dyeing acid modified polyacrylonitrile, polyester and polyamide fibers.

2. Description of the Prior Art

A number of blue cationic dyes of naphthostyril series with a high fastness to heat have been known; none of them, however, are satisfactory as a three-primary color dye which is in large demand. While the well known dyes disclosed in Japanese Patent Publication No. 20714/1966 or 30070/1970 can dye polyacrylonitrile fibers a clear blue shade with high fastness, they have disadvantages in that the high dyeing velocity thereof deteriorates the compatibility which is one of the most important properties of cationic dyes. Therefore an improvement in the dyeing velocity of those blue dyes has been a serious problem in the field of dyeing.

SUMMARY OF THE INVENTION

The inventors have made extensive studies on the development of the blue dyes which are highly resistant to heat and are capable of employment as a three-primary color dye which is in a large demand, and found that dyes prepared by first condensing anilines having an N-acyloxyalkyl group with N-alkylnaphthostyrils and then hydrolyzing the N-acyloxyalkyl group of the resulting compounds in an acid state, have extremely superior properties and that such dyes can never be obtained by using, from the beginning, compounds having a hydroxyl group not protected with an acyl group in place of N-acyloxyalkyl compounds, and finally completed the present invention.

The present invention is to provide novel dyes of the following formula (I):

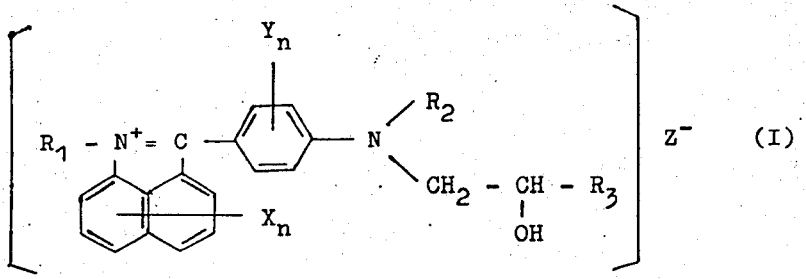

wherein
R$_1$ is a C$_1$–C$_4$ alkyl or C$_1$–C$_2$ alkoxy- or cyano-substituted C$_1$–C$_4$ alkyl,
R$_2$ is a C$_1$–C$_4$ alkyl, phenyl, C$_1$–C$_4$ alkoxy-substituted phenyl, C$_7$–C$_8$ aralkyl or cyclophenyl,
R$_3$ is a C$_1$–C$_4$ alkyl, C$_1$–C$_4$ alkoxy-substituted C$_1$–C$_2$ alkyl or phenoxy-substituted C$_1$–C$_2$ alkyl,
X is hydrogen, a halogen or N,N—di—C$_1$–C$_4$ alkylsulfonamide,
Y is hydrogen, a C$_1$–C$_2$ alkyl or a halogen,
n is an integer of from 1 to 2, and
Z$^-$ is an anion,
and their preparation and a method for dyeing various fibers with said novel dyes.

The present invention relates to heat-resistant blue cationic dyes of the formula (I), which are characterized in that a hydroxyl group is located at a β-position of the alkyl group in the aniline component. An introduction of the hydroxy group imparts, as shown below, to the present dyes effective properties distinguishable from that of conventional dyes.

One of the properties of a cationic dye required for dyeing acrylic fibers is that the dye can be employed as a so-called three-primary color dye, in other words, it can be used together with dyes of different colors to obtain intermediate colors.

When a dye having an extremely high velocity of dyeing is employed for acrylic fibers, the dyed material obtained tends to be uneven, particularly when intermediate or light colors are required, because only the absorption of the dye proceeds rapidly when a temperature of dyebath is raised above a predetermined temperature.

Accordingly, in order to obtain articles colored uniformly an intermediate color by the co-use of dyes of different colors, it is required that each dye shows the proper dyeing velocity and the difference in dyeing velocity between or among the dyes is not so large. According to the present invention, dyes having proper dyeing velocity in such cases can be provided.

It is known that when dyeing acrylic fibers with cationic dyes, the dyed material can be provided with a high fastness to light and hot water and an excellent vividness, especially when the so-called conjugated type cationic dyes are used.

But when these dyes are used in dyeing other synthetic fibers such as polyester fibers, the dyed material can be provided with vividness, but its light fastness is poor. On the other hand, a relatively high light fastness is obtained when dyed with disperse dyes, but the same vividness as obtained with cationic dyes can hardly be obtained.

The dyes of the invention provide a higher light-fastness then conventional cationic dyes of naphthostyril series and the tendency is more marked when the fibers are dyed in light colors.

In particular, when fibers are dyed light blue by known dyes of naphthostyril series, the fibers thus dyed are faded greatly by sunlight and hence the dyeing is unsatisfactory.

Furthermore, the dyes of the present invention have a remarkable feature that, when they are employed together with dyes of different colors to dye modified polyester fibers, they give an appropriate dyeing velocity to permit the absorption thereof to proceed at approximately the same rate as that of other dyes. Such an excellent property of the dyes of the invention suitable for an acid-modified polyester fiber can hardly be obtained with known dyes.

In other words, such a property is also one of the most important features of the dyes of the invention having a β-hydroxy-substituted alkyl group, as shown in the formula (I).

The dyes of naphthostyril series can generally impart a very clear shade and a high fastness to heat; however, they can not impart a high fastness to light and a compatibility at the same time. The dyes disclosed in Japanese Patent Publication No. 30070/1970 have an increased fastness to light by introducing a cyanoethyl or carbamoylethyl group into $R_1$ of the formula (I), while they still have a problem of compatibility, as mentioned hereinbefore, to be used as a three-primary color dye. According to the present invention, there is provided general purpose cationic dyes of naphthostyril series which have a fastness to heat not deteriorated and can also be used as a three-primary color dye.

A method of the present invention can be achieved by first preparing compounds of the formula (IV):

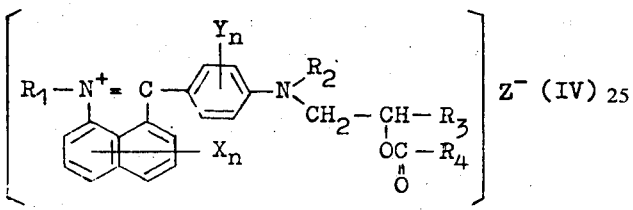

wherein
$R_1$, $R_2$, $R_3$, X, Y, $n$ and $Z^-$ are as defined above, and $R_4$ represents an alkyl group having from 1 to 3 carbon atoms,
by reacting N-alkylnaphthostyril of the formula (II):

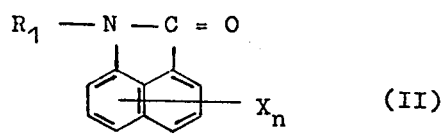

wherein $R_1$, X and $n$ are as defined above, with compounds of the formula (III):

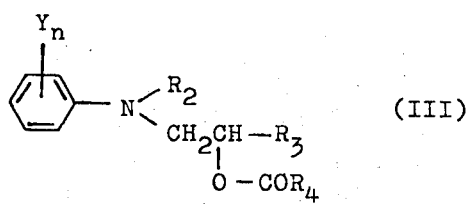

wherein $R_2$, $R_3$, $R_4$, Y and $n$ are as defined above, in the presence of a condensing agent and then by hydrolyzing the resulting compound of the formula (IV) in an acid condition to give valuable novel dyes of the formula (I).

The present invention will be illustrated in detail as follows.

DETAILED DESCRIPTION OF THE INVENTION

As examples of N-alkylnaphthostyrils of the formula (II), N-methylnaphthostyril, N-ethylnaphthostyril, N-n-propylnaphthostyril, N-butylnaphthostyril, N-methoxyethylnaphthostyril, N-ethoxyethylnaphthostyril, N-cyanoethylnaphthostyril, and their derivatives such as 6-chloro-, 6-bromo-, 6,8-dichloro-, 6,8-dibromo-, 6-N,N-dimethylsulfonamide-, 6-N,N-diethylsulfonamide-, and 6-N,N-dibutylsulfonamide-derivatives can be employed. Particularly N-methoxyethylnaphthostyril, N-ethoxyethylnaphthostyril and their halogenated derivatives are preferably employed.

As examples of N,N-dialkylanilines of the general formula (III), N-methyl-N-β-acetoxypropylaniline, N-ethyl-N-β-acetoxypropylaniline, N-propyl-N-β-acetoxypropylaniline, N-butyl-N-β-acetoxypropylaniline, N-methyl-N-propionyloxypropylaniline, N-ethyl-N-propionyloxypropylaniline, N-propyl-N-propionyloxypropylaniline, N-butyl-N-propionyloxybutylaniline, N-methyl-N-butyryloxypropylaniline, N-ethyl-N-butyryloxypropylaniline, N-propyl-N-butyryloxypropylaniline, N-ethyl-N-β-acetoxybutylaniline, N-ethyl-N-β-propionyloxypropylaniline, N-ethyl-N-β-butyryloxybutylaniline, N-methyl-N-β-acetoxy-γ-methoxypropylaniline, N-ethyl-N-β-acetoxy-γ-methoxypropylaniline, N-methyl-N-β-acetoxy-γ-butoxypropylaniline, N-ethyl-N-β-acetoxy-γ-butoxypropylaniline, N-methyl-N-β-acetoxy-γ-phenoxypropylaniline, N-p-methoxyphenyl-N-acetoxypropylaniline, N-benzyl-N-acetoxypropylaniline, N-cyclohexyl-N-acetoxybutylaniline, N-ethyl-N-β-acetoxypropyl-m-toluidine, N-ethyl-N-acetoxypropyl-m-chloroaniline, N-methyl-N-β-acetoxy-γ-methylthiopropylaniline and N-methyl-N-β-acetoxy-γ-butylthiopropylaniline are preferably employed.

According to the present invention, compounds of the formula (II) are reacted with compounds of the formula (III) in an inert solvent in the presence of a condensing agent or in an excess of a condensing agent, and the reaction generally proceeds substantially completely at 80° to 120°C of reaction temperature for about 5 to 10 hours of reaction time. It is sufficient that an amount of inert solvents employed in the reaction is one to three times by weight the total amount of both compounds (II) and (III), and the solvents which can be employed are benzene, toluene, xylene, monochlorobenzene, dichlorobenzene, chlorotoluene, nitrotoluene and nitrobenzene.

The reaction is a dehydration-condensation reaction, and so care must be taken to keep the reaction system free from water. Condensing agent which can be employed are phosphorus oxychloride, phosphorus oxybromide, phosphorus trichloride, phosphorus pentachloride, thionylchloride, sulfurylchloride, titanium trichloride and stannic chloride, each of which is employed in an amount of one to five times by mole based on the compounds (II).

Furthermore, as a reaction-accelerating agent phosphorus pentoxide and polyphosphoric acid may preferably to employed. In order to obtain good levelling dyes aimed by the present invention from compounds of the formula (IV) prepared according to the present invention, the ester group of the compounds (IV) is hydrolyzed by pouring the reaction mixture containing the compounds (IV) into water followed by heating while stirring. Alternatively the hydrolysis can also be carried out by isolating the compounds of the formula (IV) once from the reaction medium, dissolving the compounds in water and then heating in the presence of an acid. The novel dyes of the formula (I) thus obtained have a high solubility in water and a clear blue shade. The dyes of the formula (I) can be isolated in the form of crystals by conventional methods such as salting-out from the solution after reaction.

The present invention will now concretely be illustrated with reference to the following examples. The parts indicated in the examples are parts by weight, unless otherwise stated.

EXAMPLE 1

12.2 parts of N-methoxyethyl-6-bromonaphthostyril, 8.9 parts of N-methyl-N-β-acetoxybutylaniline and 10 parts of polyphosphoric acid (content of P₂O₅ is 84%) are dissolved in 30 parts of monochlorobenzene under heating. 24 parts of phosphorus oxychloride are added dropwise to the resulting solution of 90° to 100°C which is subsequently subjected to a condensation reaction at 100° to 110°C for about 6 to 7 hours while stirring, when the solution becomes deep blue. After the reaction is completed, monochlorobenzene is recovered by water distillation with which a hydrolysis reaction is accompanied owing to an acidity of the medium to cut off an ester linkage of the resulting compound. After the completion of the water distillation, 1 part of active carbon is added thereto while hot, and the solution is allowed to cool down to about 30° to 40°C and then filtered. The filtrate is made up to about 200 c.c. and is salted out by the addition of 30 parts of sodium chloride according to a conventional process to give a dye of the formula as shown below. The dye dyes fibers of polyacrylonitrile series a clear blue shade, and the dyed material has a high fastness to light and heat.

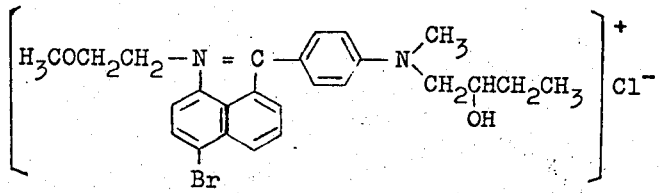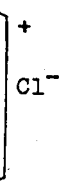

EXAMPLE 2

12.2 parts of N-methoxyethyl-6-bromonaphthostyril and 9.5 parts of N-ethyl-N-β-acetoxybutylaniline are dissolved in 30 parts of monochlorobenzene under heating. 24 parts of phosphorus oxychloride are added dropwise to the resulting solution at 100° to 110°C which is subsequently subjected to a condensation reaction at 100° to 110°C for about 6 to 7 hours while stirring, when the solution becomes deep blue. Monochlorobenzene is recovered by water distillation with which a hydrolysis reaction is accompanied owing to an acidity of the medium to cut off an ester linkage of the resulting compound. After the water distillation is completed, 1 part of active carbon is added thereto while hot, and the solution is allowed to cool down to about 30° to 40°C and then filtered. The filtrate is made up to about 200 c.c. and is salted out by the addition of 30 parts of sodium chloride according to a conventional process to give a dye of the formula as shown below. The dye dyes fibers of polyacrylonitrile series a clear blue shade and the dyed material has a high fastness to light and heat.

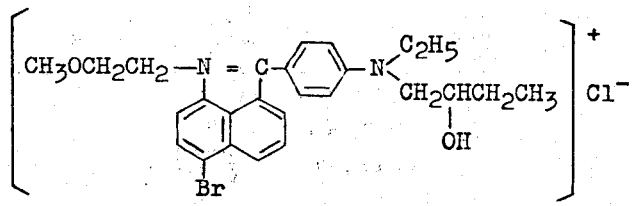

EXAMPLE 3

8.7 parts of N-methyl-6-chloronaphthostyril, 8.3 parts of N-ethyl-N-β-acetoxypropylaniline and 5 parts of phosphorus pentoxide are dissolved in 30 parts of monochlorobenzene under heating. 24 parts of phosphorus oxychloride is added dropwise to the resulting solution at 90° to 100°C which is subsequently subjected to a condensation reaction at 100° to 110°C for about 8 hours, when the solution becomes deep blue. The solution is treated as described in Example 1 to give a dye imparting fibers of polyacrylonitrile series a clear blue shade as shown in the following formula.

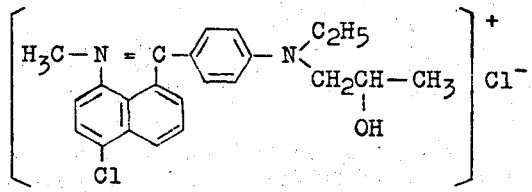

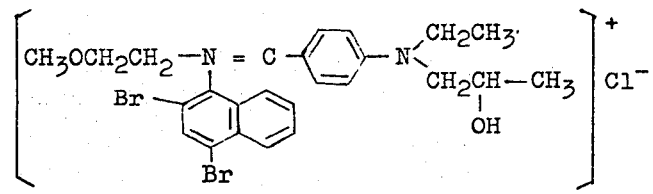

EXAMPLE 4

15.4 parts of N-methoxyethyl-6,8-dibromonaphthostyril, 8.9 parts of N-ethyl-N-β-acetoxypropylaniline, 30 parts of monochlorobenzene and 24 parts of phospho-

EXAMPLES 5 – 21

The dyes as shown in Table are obtained by the way similar to that described in Example 1.

Table

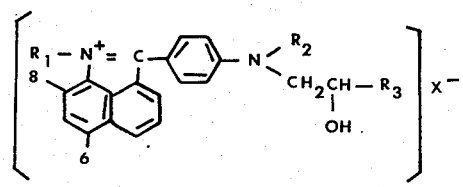

| Compound No. | $R_1$ | $R_2$ | $R_3$ | Naphthostyril Nucleus * | Benzene Nucleus ** | $X^-$ | Shade of Polyacrylonitrile Fibers |
|---|---|---|---|---|---|---|---|
| 5 | —CH$_2$CH$_2$OCH$_3$ | C$_2$H$_5$ | CH$_3$ | 6,8-dichloro- | H | Cl | blue |
| 6 | " | " | " | 6-bromo- | " | " | " |
| 7 | —CH$_2$CH$_2$OC$_2$H$_5$ | " | " | 6,8-dibromo- | " | " | " |
| 8 | —CH$_2$CH$_2$OCH$_3$ | ⌬-OCH$_3$ | " | 6,8-dichloro- | " | " | reddish blue |
| 9 | " | C$_2$H$_5$ | " | 6-chloro- | m-methyl | " | blue |
| 10 | —CH$_2$CH$_2$CN | ⌬H | " | H | m-chloro | " | reddish blue |
| 11 | —CH$_3$ | " | " | 6-chloro | " | " | blue |
| 12 | " | C$_4$H$_9$ | " | 6-chloro | " | " | " |
| 13 | " | C$_2$H$_5$ | C$_2$H$_5$ | 6-bromo | " | " | " |
| 14 | —C$_2$H$_5$ | CH$_3$ | C$_2$H$_5$ | 6,8-dibromo | " | " | " |
| 15 | —C$_2$H$_5$ | C$_2$H$_5$ | CH$_3$ | 6,8-dibromo | " | " | " |
| 16 | —C$_2$H$_5$ | C$_2$H$_5$ | CH$_2$O-⌬ | 6-N,N-diethyl-sulfonamide | H | " | " |
| 17 | —CH$_2$CH$_2$OCH$_3$ | C$_4$H$_9$ | CH$_2$O-⌬ | 6-N,N,-diethyl-sulfonamide | H | " | " |
| 18 | " | " | CH$_2$OCH$_3$ | 6-chloro | " | " | " |
| 19 | " | " | CH$_2$OC$_4$H$_9$ | " | " | " | " |
| 20 | —C$_2$H$_5$ | C$_2$H$_5$ | CH$_2$OC$_2$H$_5$ | 6-bromo | " | " | " |
| 21 | —CH$_2$CH$_2$OCH$_3$ | " | " | " | " | " | " |

Remark
* a number indicates a position at which a substituent is linked to a naphthostyril nucleus, and H indicates no substitution at the position.
** H indicates no substitution and a symbol indicating a position of substitution is based on the position of the nitrogen atom linked to the benzene nucleus.

rus oxychloride are treated in the same manner as described in Example 1 to give a dye giving fibers of polyacrylonitrile series a clear blue shade as shown in the following formula.

EXAMPLE 22

In a 300 c.c. pot are placed 0.05 part of a dye of the following formula which is one of the most common yellow cationic dyes,

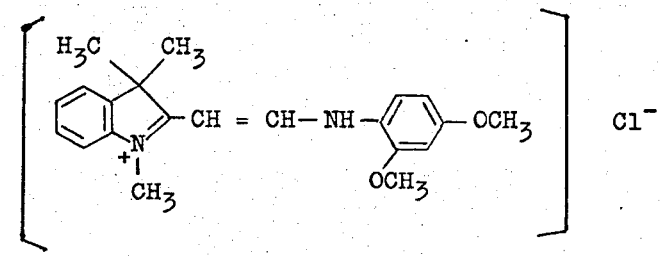

0.05 part of the dye obtained in Example 1 and 0.11 part of Ospin TAN (a product from Tōkai Seiyu Co. Ltd.) as a levelling agent. 0.05 part of acetic acid, 0.025 part of sodium acetate and 250 parts of water are further added thereto to prepare a dyebath which is adjusted to 4.5 of pH. Separately from this, a dyebath is prepared in the same way as described above except that a well-known dye of the following formula is employed in place of the dye obtained in Example 1. Four dyebaths of each preparation above mentioned are prepared. Eight pots containing the dyebaths thus prepared are maintained at 98°C of a constant temperature in a boiling water-bath, and then 5 parts of Cashmilon F high bulky yarn (a product from Asahi Kasei Co. Ltd.) are introduced in each of dyebaths to start a dyeing. The dyeing is carried out in such a way that the yarn can always be shaken and is removed out of a pot one by one 5, 10, 20 and 60 minutes after the beginning of dyeing with each preparation. Then a dyebath is cooled to 60°C after the removal of fiber, and another 5 parts of Cashmilon F high bulky yarn are placed therein and dyed.

By the comparison between the yarns dyed according to the two preparations, it can be observed that the former preparation gives no change in a green shade except that the shade becomes deeper as a dyeing time becomes longer in order of 5, 10 and 20 minutes, and also gives no change in a green shade, with the second yarns dyed in residual baths from which the first yarns have been removed, except that the shade becomes lighter with a lapse of dyeing time. On the other hand, the yarns dyed according to the latter preparation employing the well-known dye are blue in shade while a dyeing time is short; however, they become green by a rapid absorption of the yellow dye with a lapse of a dyeing time.

The change not only in depth but also in shade in a dyeing process as seen in the latter preparation employing the well-known dye is not desirable because it often causes an unlevelness of dyeing.

While the invention has been described in detail and with reference to specific embodiments thereof, it will be apparent to one skilled in the art that various changes and modifications can be made therein without departing from the spirit and scope thereof.

What we claim is:

1. A compound of the formula

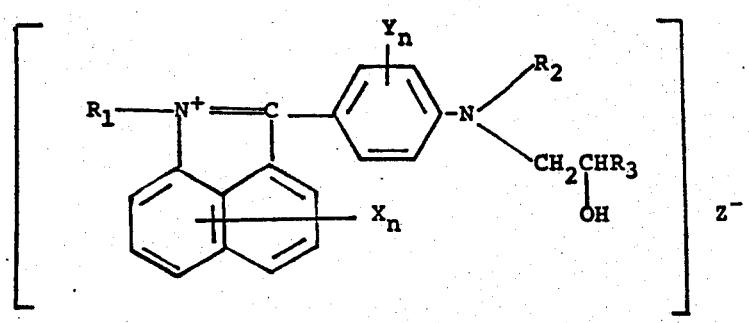

wherein $R_1$ is $\beta$-$C_1$-$C_2$ alkoxy substituted ethyl, $R_2$ is $C_1$-$C_4$ alkyl or phenyl substituted by one $C_1$-$C_2$ alkoxy, $R_3$ is $C_1$-$C_4$ alkyl or $C_1$-$C_2$ alkyl substituted by one $C_1$-$C_4$ alkoxy, X is hydrogen or halogen, Y is hydrogen, a $C_1$-$C_2$ alkyl or a halogen, $n$ is an integer of from 1 to 2, and $Z^-$ is an anion.

2. The compound according to claim 1, wherein $R_2$ is $C_1$-$C_4$ alkyl.

3. The compound according to claim 1, wherein $R_3$ is $C_1$-$C_4$ alkyl.

4. The compound represented by the formula:

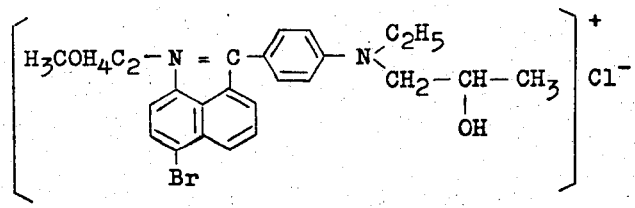

5. The compound represented by the formula:

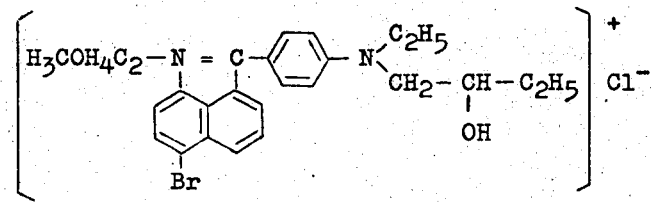

* * * * *